US011730777B2

(12) United States Patent
Thoral et al.

(10) Patent No.: US 11,730,777 B2
(45) Date of Patent: Aug. 22, 2023

(54) MUCOADHESIVE SUSTAINED-RELEASE VAGINAL TABLET

(71) Applicant: BIOSE, Arpajon-sur-Cere (FR)

(72) Inventors: Claudia Thoral, Massiac (FR); Pierre Tchoreloff, Gradignan (FR); Vincent Mazel, Mérignac (FR); Virginie Busignies, Mérignac (FR); Adrien Nivoliez, Yolet (FR)

(73) Assignee: NEXBIOME THERAPEUTICS, Clermont-Ferrand (FR)

( * ) Notice: Subject to any disclaimer, the term of this patent is extended or adjusted under 35 U.S.C. 154(b) by 952 days.

(21) Appl. No.: 16/451,881

(22) Filed: Jun. 25, 2019

(65) Prior Publication Data

US 2020/0155621 A1    May 21, 2020

Related U.S. Application Data

(63) Continuation of application No. 15/124,148, filed as application No. PCT/EP2015/054918 on Mar. 10, 2015, now abandoned.

(30) Foreign Application Priority Data

Mar. 10, 2014   (FR) ..................................... 1451951

(51) Int. Cl.
  *A61K 35/747*  (2015.01)
  *A61K 9/00*    (2006.01)
  *A61K 9/20*    (2006.01)
  *A61K 9/02*    (2006.01)

(52) U.S. Cl.
  CPC .......... *A61K 35/747* (2013.01); *A61K 9/0034* (2013.01); *A61K 9/02* (2013.01); *A61K 9/2054* (2013.01)

(58) Field of Classification Search
  CPC ...... A61K 35/747; A61K 9/0034; A61K 9/02; A61K 9/2054; A61P 15/02
  See application file for complete search history.

(56) References Cited

U.S. PATENT DOCUMENTS

| 8,007,777 B2 | 8/2011 | Borek et al. | |
| 2013/0171253 A1* | 7/2013 | Kiss | A61P 31/04 424/452 |

FOREIGN PATENT DOCUMENTS

| AU | 2011202580 A1 * | 6/2011 | ............... A61K 9/16 |
| EP | 1500394 A1 | 1/2005 | |
| WO | 03/026687 A1 | 4/2003 | |
| WO | 2013/093941 A2 | 6/2013 | |
| WO | 2013/118092 A1 | 8/2013 | |

OTHER PUBLICATIONS

International Search Report for Application No. PCT/EP2015/054918 dated May 15, 2015.
Written Opinion of International Application No. PCT/EP2015/054918 dated May 15, 2015.
Valenta, C., "The use of mucoadhesive polymers in vaginal delivery," Advanced Drug Delivery Reviews 57, Sep. 22, 2005, DD. 1692-1712.
Coudeyras, S. et al., "Adhesion of Human Probiotic Lactobacillus rhamnosus to Cervical and Vaginal Cells and Interaction with Vaginosis-Associated Pathogens," Infectious Diseases in Obstetrics and Gynecology, vol. 2008, Article ID 549640, oo. 1-5.
Nivoliez, A. et al., "Influence of manufacturing processes on in vitro properties of the probiotic strain Lactobacillus rhamnosus Lcr35," Journal of Biotechnology, 2012, six pages.
Ehrstrom, S. et al., "Lactic acid bacteria colonization and clinical outcome after probiotic supplementation in conventionally treated bacterial vaginosis and vulvovaginal candidiasis," Microbes and Infection 12 , May 28, 2012, oo. 691-699.
Ahmad, F. J. et al., "Development and in vitro evaluation of an acid buffering bioadhesive vaginal gel for mixed vaginal infections," Acta Pharm. 58, 2008, oo. 407-419.
Fazeli, M.R. et al., "Viability of lactobacillus acidophilus in various vaginal tablet formulations," DARU vol. 14, No. 4, May 3, 2006.
Anonymous, "Gy-Na-Tren Vaginal Health Solution by Natren," www.rockwellnutrition.com, Oct. 20, 2010, three oacies.
Maggi, L. et al., "Technological and biological evaluation of tablets containing different strains of lactobacilli for vaginal administration," European Journal of Pharmaceutics and Biopharmaceutics 50, Aug. 10, 2000, DD. 389-395.
Mohammed, A., "Preparation and characterization of a coacervate extended-release microparticulate delivery system for Lactobacillus rhamnosus," International Journal of Nanomedicine, 2011, DD. 1699-1707.
Nader-Macias, M. et al., "Advances in the Knowledge and Clinical Applications of Lactic Acid Bacteria as Probiotics in the Urogenital Tract," Current Women's Health Reviews, vol. 4, No. 4 (2008), 00. 240-257.
Anonvmous, "Pro Thera—Ther-Biotic," www.protherainc.com, Jun. 24, 2009, two pages.
Vicariotto, F. et al., "Effectiveness of the Association of 2 Probiotic Strains Formulated in a Slow Release Vaginal Product, in Women Affected by Vulvovaginal Candidiasis," Journal of Clinical Gastroenterology, Oct. 2012, pp. S73-S80.
Mastromarino, P. et al., "Effectiveness of Lactobacillus-containing vaginal tablets in the treatment of symptomatic bacterial vaginosis", Clinical Microbiology and Infection, Jan. 2009, pp. 67-74, vol. 15, No. 1.

(Continued)

*Primary Examiner* — Lynn Y Fan (74) *Attorney, Agent, or Firm* — McBee Moore & Vanik IP, LLC; Susan E. Shaw McBee (57) ABSTRACT

The disclosure relates to a mucoadhesive sustained-release vaginal tablet including at least one probiotic strain of the genus *Lactobacillus* compressed with an excipient suitable for conferring upon the tablet the properties of vaginal wall mucoadhesion and sustained release.

5 Claims, 4 Drawing Sheets

(56) References Cited

OTHER PUBLICATIONS

Karasulu, H.Y. et al., "Sustained release bioadhesive effervescent ketoconazole microcapsules tabletted for vaginal delivery", Journal of Microencapsulation, 2002, pp. 357-362, vol. 19, No. 3.
Patel, Anita et al., "Development and Evaluation of Mucoadhesive Vaginal Tablet of Sertaconazole for Vaginal Candidiasis", International Journal of PharmTech Research, Oct.-Dec. 2011, pp. 2175-2182, vol. 3, No. 4.
Gavini, Elisabetta et al., "Mucoadhesive Vaginal Tablets as Veterinary Delivery System for the Controlled Release of an Antimicrobial Drug, Acriflavine", AAPS PharmSci, 2002, pp. 1-7, vol. 3, No. 3.
Klayraung, Srikanjana et al., "Development of tablets containing probiotics: Effects of formulation and processing parameters on bacterial viability", International Journal of Pharmaceutics, 2009, pp. 54-60, vol. 370.

\* cited by examiner

MUCOADHESIVE SUSTAINED-RELEASE VAGINAL TABLET

CROSS-REFERENCE TO RELATED APPLICATIONS

This application is a continuation of U.S. patent application Ser. No. 15/124,148, filed 7 Sep. 2016, which is a National Phase Entry of International Patent Application No. PCT/EP2015/054918, filed on Mar. 10, 2015, which claims priority to French Patent Application Serial No. 1451951, filed on Mar. 10, 2014, both of which are incorporated by reference herein.

FIELD OF THE INVENTION

The present invention relates to a mucoadhesive sustained-release vaginal tablet particularly useful in the treatment of vaginal infections, vaginoses, in particular vulvovaginal candidiases or recurrent vulvovaginal candidiase.

BACKGROUND OF THE INVENTION

Vulvovaginal candidiasis (VVC) is a mycotic infection affecting nearly 70-75% of women of child-bearing age. About 40-50% of these will have a relapse. In turn, between 5% and 8% of women are affected by a recurrent VVC (at least four episodes per year). The pathogenic agent responsible for these candidiases is generally *Candida albicans*.

In healthy women, the urogenital flora comprises nearly 50 different species of microorganisms. Among these microorganisms, 95% of the population is composed of various strains of lactobacilli, also called "Doderlein's bacilli", which are indicators of healthy vaginal flora. These lactobacilli play a protective role against pathogens by various mechanisms: production of hydrogen peroxide, lactic acid and bacteriocins, inhibition of pathogen adhesion and expansion. In particular, these lactobacilli maintain an acidic pH (in particular between 4.5 and 5) by producing lactic acid from the glycogen present in the vaginal mucus. Thus, the growth of many pathogens of the vaginal flora, such as *Gardnerella vaginalis*, *Prevotella bivia*, *Atopobium vaginae*, *Neisseria gonorrhoeae*, *Mycoplasma*, *Mobiluncus* and especially *Candida albicans*, is inhibited thanks to this environment unfavorable to their development. Normal vaginal flora is thus principally composed of lactobacilli forming a protective biofilm on the surface of the mucous membrane. The lactobacilli specific to the vagina are in particular *Lactobacillus* crispatus, *Lactobacillus* jensenii and *Lactobacillus* vaginalis. The development of vulvovaginal candidiases seems to be promoted by a loss of balance of the urogenital flora observed in particular by a decrease in the population of lactobacilli inducing colonization of the medium by a pathogen.

VVC, particularly recurrent VVC, negatively affects the well-being of certain women. Its treatment generates significant healthcare expenditures and proves to be difficult because of the multifactorial pathogenesis of this illness (antibiotic treatments, pregnancy, stress, etc.). Typically, VVC is treated by means of antifungal active agents administered systemically or locally. Current treatments prove to be constraining, in particular local treatments (vaginal suppositories). Indeed, the dosage of antifungals administered locally is generally daily, which translates to lower compliance and thus to increased risks of recurrence. In addition, the side effects of antifungals can lead to a disturbance of the normal vaginal flora, thus increasing the risks of recurrence by destruction of the natural flora. Antifungal active agents are also likely to generate irritation and vaginal dryness phenomena associated with an unpleasant sensation of discharge when the vaginal suppositories melt.

A need thus exists for the provision of means for effectively treating VVC and for increasing patient well-being so as to limit problems of compliance and thus to reduce recurrences, particularly for effectively treating VVC by means of probiotics.

BRIEF DESCRIPTION OF THE INVENTION

The present invention relates to a mucoadhesive sustained-release vaginal tablet comprising at least one probiotic strain of the genus *Lactobacillus* compressed with an excipient suitable for conferring upon said tablet the properties of vaginal wall mucoadhesion and sustained release. The excipient is present in an amount that allows both good adhesion to the mucous membranes and sustained release of the strain. The sustained release must meet the two requirements of ensuring the viability of the strain and allowing the tablet to be administered over time. Indeed, what is sought is a treatment that allows administration of at most one tablet every two days, advantageously at most every three days or more.

The present invention relates to a method for preparing a mucoadhesive sustained-release vaginal tablet comprising the following steps:
 a. Mixing at least one probiotic strain of the genus *Lactobacillus* with an excipient suitable for conferring upon said tablet the properties of vaginal wall mucoadhesion and sustained release;
 b. Compressing the mixture obtained in step a. with a compressive stress of 50 to 400 MPa.

The present invention also relates to the use of said tablet in the treatment of vaginal infections, vaginoses.

DEFINITIONS

The term "CFU" refers to the measurement unit recognized by the person skilled in the art for quantifying bacteria capable of founding a colony and precisely means "Colony Forming Unit".

The term "API" means "Active Pharmaceutical Ingredient", also called active substance.

The term "probiotic" refers to living microorganisms that when administered in sufficient quantities confer a beneficial effect upon health of the host.

The expression "properties of vaginal wall mucoadhesion" is defined as being the adhesion of two surfaces one of which is an epithelium. The properties of vaginal wall mucoadhesion can be determined by various methods, as described in the reference European Journal of Pharmaceutics and Biopharmaceutics, 85, (2013) 843-853. In particular, the properties of vaginal wall mucoadhesion can be evaluated by determining the time or the force necessary to detach a dosage form from a mucous membrane.

The expression "sustained-release tablet" refers to a tablet in which the rate of release of the active substance is slowed down, the release of the active substance being spread out over time (as opposed to "flash" immediate release). Preferably, the expression "sustained-release tablet" refers to a tablet ensuring the diffusion of the active ingredient over a longer duration than the conventional release often comparable to a flash dose.

DETAILED DESCRIPTION OF THE INVENTION

The Inventors developed a dosage form including probiotics making it possible to combine treatment efficacy and woman well-being when taking probiotics, leading advantageously to increased compliance with the treatment of vaginal infections, vaginoses, in particular VVC, and thus avoiding a recurrence thereof.

The invention thus relates to a mucoadhesive sustained-release vaginal tablet comprising at least one probiotic strain of the genus *Lactobacillus* compressed with an excipient suitable for conferring upon said tablet the properties of vaginal wall mucoadhesion and sustained release. The mucoadhesive sustained-release vaginal tablet can comprise one or more probiotic strains of the genus *Lactobacillus*.

The dosage form developed by the Inventors allows sustained-release of a *lactobacillus* strain while integrating properties of vaginal wall mucoadhesion, limiting patient inconvenience, and of sustained release, thus overcoming the problems of dosage and risk of recurrence (associated with pathogen resistance). The tablet of the present invention is intended for local administration. The application could be carried out by the patient or by means of an applicator adapted to the form of the tablet to facilitate the administration thereof.

The administration of probiotic strains of the genus *Lactobacillus* is known to promote vaginal health. In particular, probiotic strains of the genus *Lactobacillus* useful for treating vaginal infections, vaginoses, in particular VVC and for preventing the recurrence thereof can be as described in WO 2014/009349.

The mucoadhesive sustained-release vaginal tablet according to the present invention preferably comprises a probiotic strain of the genus *Lactobacillus* selected from *Lactobacillus rhamnosus*, *Lactobacillus crispatus*, *Lactobacillus iners*, *Lactobacillus gasseri*, *Lactobacillus jensenii*, *Lactobacillus acidophilus*, *Lactobacillus plantarum*, *Lactobacillus vaginalis*, *Lactobacillus casei*, *Lactobacillus reuteri* and combinations thereof, in particular in pairs. Preferably, the probiotic strain of the genus *Lactobacillus* is Lcr35® (*Lactobacillus rhamnosus*). In another variant, the probiotic strain of the genus *Lactobacillus* is the *Lactobacillus* crispatus IP174178 strain deposited with the NCMC under number 1-4646. In another variant, a combination of *Lactobacillus* crispatus and *Lactobacillus rhamnosus* (advantageously Lcr35®) is used.

The mucoadhesive sustained-release vaginal tablet according to the present invention generally comprises from $10^5$ to $10^{11}$ CFU of the probiotic strain of the genus *Lactobacillus*, preferably from $10^9$ to $10^{10}$ CFU of said strain, per gram of tablet. Typically, the mucoadhesive sustained-release vaginal tablet according to the present invention comprises from $10^9$ to $10^{11}$ CFU of the probiotic strain of the genus *Lactobacillus* per gram of tablet after manufacture (content measured the day of manufacture). Typically, the mucoadhesive sustained-release vaginal tablet according to the present invention comprises at least $10^7$ CFU of the probiotic strain of the genus *Lactobacillus* strains per gram of tablet after storage for 36 months at 25° C. When a combination of strains is used, each strain is present at such concentrations.

Advantageously, the tablet according to the present invention makes it possible to retain the dose of the probiotic strain while spreading out the release of said dose over time. This makes it possible to decrease the dosage in order to improve patient compliance while extending the duration of the therapeutic effect in order to avoid a recurrence. The probiotic strain of the genus *Lactobacillus* is preferably in freeze-dried form. Before lyophilization, the strain is advantageously mixed with cryoprotectants in order to provide it with very high stability at room temperature. For example, the strain can be mixed with an alkali or alkaline-earth metal thiosulfate (FR 1 426 226), advantageously sodium thiosulfate.

The mucoadhesive sustained-release vaginal tablet according to the present invention comprises an excipient suitable for conferring upon said tablet the properties of vaginal wall mucoadhesion and sustained release. Such excipients are known to the person skilled in the art. Examples of suitable excipients are described in Advanced Drug Delivery System Reviews, 57 (2005), 1692-1712. The excipient can be selected from chitosan and derivatives thereof, pectins, polyethylenes glycols, sodium alginate, polyacrylic acids, cellulose derivatives such as sodium carboxymethylcellulose, hydroxypropylmethylcellulose or microcrystalline cellulose, gums, Carbopol® and combinations thereof. Preferably, the tablet according to the present invention comprises a cellulose derivative, in particular hydroxypropylmethylcellulose (HPMC).

In the context of the invention, high viscosity hydroxypropylmethylcellulose is preferably used. Thus, hydroxypropylmethylcellulose advantageously having a dynamic viscosity greater than 10,000 mPa·s, advantageously between 11,000 mPa·s and 21,000 mPa·s, more advantageously about 15,000 mPa·s, is used. The viscosity of this well-known excipient is measured according to the European or American standard for a 2% (w/v) aqueous solution of hydroxypropylmethylcellulose at 20° C.

The mucoadhesive sustained-release vaginal tablet according to the present invention generally comprises from 10% to 40% by weight, relative to the total weight of the tablet, of an excipient conferring upon said tablet the properties of vaginal wall mucoadhesion and sustained release. Preferably, the tablet comprises from 10% to 30% by weight, relative to the total weight of the tablet, of said excipient, more advantageously from 10% to 25% by weight, even more advantageously from 10% to 20% by weight, or it comprises 10% by weight of said excipient.

Advantageously, the excipients described above allow sustained release over time of the probiotic strain. In particular, it was shown that the tablet of the present invention allows progressive release of the strain, unlike the immediate release of the strain in a medium from the commercial powder (in equivalent doses) (FIG. 1), the commercial powder being the powder contained in the capsules (capsules, Lcr Regenerans®) marketed under the name Gynophilus® by the company PROBIONOV.

Figure 2:
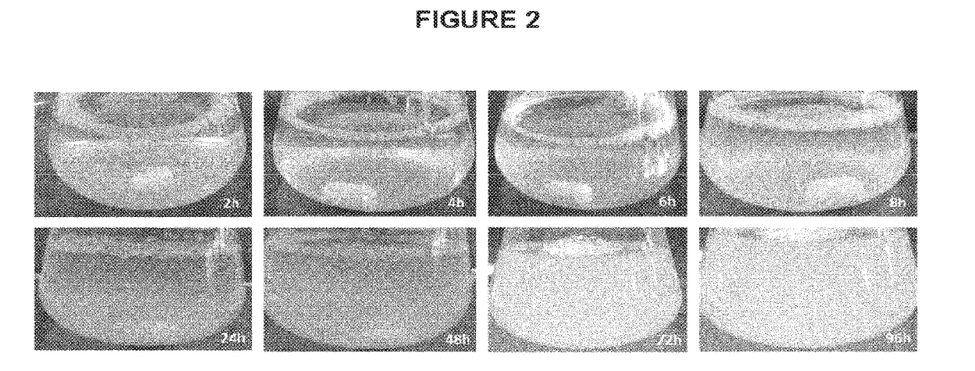
FIG. 2 represents the evolution in terms of wetting and erosion of the tablet of the present invention in SVF medium over time (96 h).

More precisely, it was shown that the tablet of the present invention leads to quantities of bacteria equivalent to the commercial powder in terms of release plateau for an initial quantity of bacteria in the dosage form on the order of $10^9$ CFU/g. In addition, it was shown that tablet wetting and erosion are spread out over at least 72 h allowing a extension of the release of the Lcr35® strain (FIG. 2).

Thus, the mucoadhesive sustained-release vaginal tablet according to the present invention can be administered every 3-7 days, i.e. a tablet every 3, 4, 5, 6 or 7 days. Typically, the capsules are administered once per day. Administration of the tablet of the present invention thus makes it possible to decrease the number of drug doses and thus to improve patient compliance. According to an advantageous variant of the invention, the tablet is intended for local administration at most every 2 days, advantageously at most every 3 days, or every 4 days, or every 5 days, or every 6 days or every 7 days.

The probiotic strain of the genus *Lactobacillus*, preferably in freeze-dried form, and the excipient conferring upon the tablet the properties of vaginal wall mucoadhesion and sustained release are compressed to give the tablet of the present invention. Preferably, the probiotic strain and the excipient are compressed with a compressive stress of 50 to 400 MPa, more particularly of 200 to 250 MPa. Preferably, the compressive stress is 250 MPa.

It is well-known that it is necessary to control the stability of any pharmaceutical formulation comprising a probiotic strain over its lifetime (from its manufacture to its consumption) so that the expected therapeutic effect can be observed. It is also known that the viability of the bacteria is sensitive to manufacturing processes (and in particular during the compression step) and to storage conditions and durations.

Figure 3:
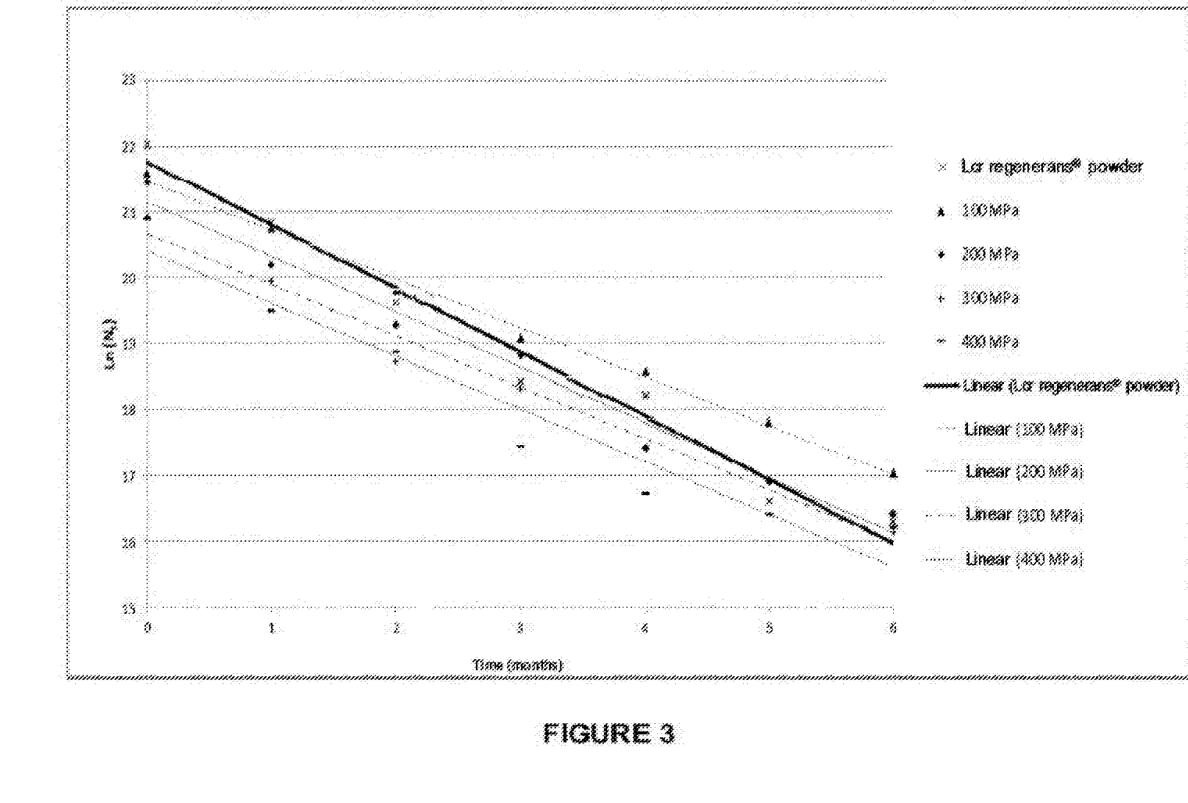
FIG. 3 represents the evolution of the viability of the Lcr35® strain (ln) as a function of time (months) under conditions of accelerated stability according to the ICH reference system (40° C.) for the free powder (x, continuous line for linear extrapolation) and for tablets containing the formulated strain (Lcr Regenerans®) obtained with various compressive stresses (100 MPa—triangle, 200 MPa—diamond, 300 MPa—plus sign, 400 MPa—minus sign).

Unexpectedly, the Inventors showed that the stress sustained by the probiotic strain during compression does not negatively affect the stability (viability) of the strain under accelerated storage conditions (40° C.). By limiting the exchange surface with the external medium, compression even makes it possible to increase the stability of the strain in relation to the free powder (lower rates of destruction for the tablets compared to the free powder) (FIG. 3).

Thus, the tablets of the present invention can guarantee the administration of a useful dose of probiotic and thus guarantee observation of the therapeutic effect sought.

The mucoadhesive sustained-release vaginal tablet according to the present invention can further comprise pharmaceutically acceptable excipients well-known to the person skilled in the art. In particular, the tablet can comprise cryoprotectants, preservatives, lubricants, flow agents, binders, diluents and combinations thereof. For example, the tablet can comprise one or more of the following excipients: inulin and derivatives thereof, maltodextrin, dextrose and derivatives thereof, fructo-oligosaccharide, starch, trehalose, glucose, magnesium stearate.

Preferably, the mucoadhesive sustained-release vaginal tablet according to the present invention further comprises between 0.1% and 99% by weight of pharmaceutically acceptable excipients well-known to the person skilled in the art relative to the total weight of the tablet.

The mucoadhesive sustained-release vaginal tablet according to the present invention can further comprise active ingredients having a complementary action. In particular, the tablet can comprise hormones (estriol, progesterone, etc.), anti-inflammatory agents, antibacterial agents and/or antifungal agents. The person skilled in the art will be able to determine which active ingredients can be advantageously combined with a probiotic strain of the genus *Lactobacillus*.

The mucoadhesive sustained-release vaginal tablet according to the present invention can be used in the prevention and/or treatment of vaginal infections.

The mucoadhesive sustained-release vaginal tablet according to the present invention can be used in the prevention and/or treatment of vaginoses.

The mucoadhesive sustained-release vaginal tablet according to the present invention can be used in the prevention and/or treatment of candidiases.

The mucoadhesive sustained-release vaginal tablet according to the present invention can be used in the prevention and/or treatment of vulvovaginal candidiases and recurrent vulvovaginal candidiases.

If need be, the mucoadhesive sustained-release vaginal tablet according to the present invention can be administered in combination with an antibiotic or antifungal treatment, or following such a treatment.

Thus, in one aspect, the present invention relates to a method for preventing and/or treating vaginal infections, vaginoses, candidiases which may be recurrent, in particular vulvovaginal candidiases or recurrent vulvovaginal candidiases, comprising the administration to a woman, by local route, of a mucoadhesive sustained-release vaginal tablet comprising a probiotic strain of the genus *Lactobacillus* compressed with an excipient suitable for conferring upon said tablet the properties of vaginal wall mucoadhesion and sustained release. The compound can be administered once every 3-7 days, i.e. one tablet every 3, 4, 5, 6 or 7 days. According to the indications (treatment of comfort, treatment of a recurrence or treatment of a recurrence and re-equilibration of the flora), the administration could be repeated two, four or six times.

Vaginal infections, candidiases and vaginoses can be any infection linked to the pathological or unbalanced growth of many parasites or pathogens of the vaginal flora, such as those of the genus *Atopobium, Candida, Gardnerella, Neisseria, Mycoplasma, Mobiluncus, Prevotella, Trichomonas*. The following species can be cited in particular: *Atopobium vaginae, Candida albicans, Gardnerella vaginalis, Neisseria gonorrhoeae, Mycoplasma hominis, Mycoplasma genitalium, Mobiluncus, Prevotella bivia, Trichomonas vaginalis*. The pathogen can be *Candida albicans*. The pathogen can be *Gardnerella vaginalis*.

Vaginosis, or bacterial vaginosis, is an imbalance of the microbial flora of the vagina. It is characterized by the disappearance of lactobacilli and the multiplication of anaerobic bacteria such as *Gardnerella vaginalis*. It reflects an imbalance of the vaginal flora.

The present invention also relates to a method for preparing a mucoadhesive sustained-release vaginal tablet comprising the following steps:
a. Mixing at least one probiotic strain of the genus *Lactobacillus* with 10% to 40% by weight, relative to the total weight of the tablet, of an excipient suitable for conferring upon said tablet the properties of vaginal wall mucoadhesion and sustained release, optionally pharmaceutically acceptable excipients and/or active ingredients having a complementary action;
b. Compressing the mixture obtained in step a. with a compressive stress of 50 to 400 MPa in order to obtain a mucoadhesive sustained-release vaginal tablet.

The probiotic strain, the excipient conferring the properties of vaginal wall mucoadhesion and sustained release, the active ingredients having a complementary action and the pharmaceutically acceptable excipients are as described above.

EXAMPLES

Study of the Viability of the Lcr35® Strain

Tablets (650 mg) containing the Lcr35® strain (API Lcr Regenerans®, 100% by weight) were manufactured with four different compressive stresses (100, 200, 300 and 400 MPa) then placed in hermetically-sealed glass pill boxes. Pill boxes containing the free powder (control) were also monitored.

According to the ICH reference system relating to the monitoring of stabilities of pharmaceutical products, the monitoring of the stability of the strain was carried out under accelerated conditions (40° C.) in order to evaluate the rate of destruction associated with each compressive stress.

Inspections were carried out at 0, 1, 2, 3, 4, 5 and 6 months. The results obtained are expressed as CFU/g. From these data, the graph of FIG. 3 was obtained by calculating the Napierian logarithm of $N_t$ (with $N_t$ the quantity of bacteria present at time t).

The rates of destruction are obtained from the slope of the line representing $\ln(N_t/N_0)$ as a function of time.

The rates of destruction associated with the study of stability under accelerated conditions for the powder and the tablets are shown in the table below:

| Compressive stress (MPa) | Rate of destruction k ($R^2$) Lcr regenerans ® |
|---|---|
| 0 | 1.0274 (0.97) |
| 100 | 0.7727 (0.99) |
| 200 | 0.9058 (0.97) |
| 300 | 0.8367 (0.97) |
| 400 | 0.9124 (0.91) |

The rates of destruction associated with the compressive stresses show a greater impact of the storage conditions on the powder (rate of destruction>1.0) compared to the tablets manufactured with the various compressive stresses (rate of destruction<0.9). Compression had no harmful effect on the capacity of the strain to be maintained under 40° C. storage conditions. The results obtained show that the stability of the strain is even improved after compression under accelerated stability conditions (decrease in exchange surface).

Preparation of the SR Tablet

The SR tablet is prepared by mixing 900 mg of API Lcr Regenerans® and 100 mg of HPMC (Metolose® 90SH-15000SR) and compressing with a compressive stress of 250 MPa.

Release of the Lcr35® Strain from the Commercial Powder (Lcr Regenerans®) and from the Tablet According to the Present Invention (SR Tablet)

The term "commercial powder" refers to API Lcr Regenerans®. Capsules comprising API Lcr Regenerans® are commercially available (Gynophilus®).

Simulated vaginal fluid medium (SVF; 250 mL) adjusted to pH 4.2 is prepared in an Erlenmeyer flask for the test. The sample is introduced into the medium at $T_0$. The Erlenmeyer flask is then placed on a stirring plate at 75 rpm, itself placed in a 37° C. oven.

At regular intervals, 1 mL of medium is sampled to carry out the quantification of the bacteria present in the SVF (counting on MRS agar) then 1 mL of fresh medium is replaced. The results obtained after monitoring for 24 hours are presented in FIG. 1.

Visual monitoring of the tablet was also carried out in this test (96 h) in order to evaluate the state of the unit in the medium. The progressive erosion of the tablet of the present invention is evaluated in hours. Complete erosion is defined by the disappearance of the compressed form to produce a suspension.

After bringing into contact 900 mg of commercial powder (amount equivalent to the amount of API present in the SR tablet) with the SVF medium, an immediate supply of the bacteria in the medium is observed. The quantity administered at $T_0$ is found at all the sampling times. This demonstrates the immediate and total release of the strain from the capsule form once the capsule dissolves.

Figure 1:
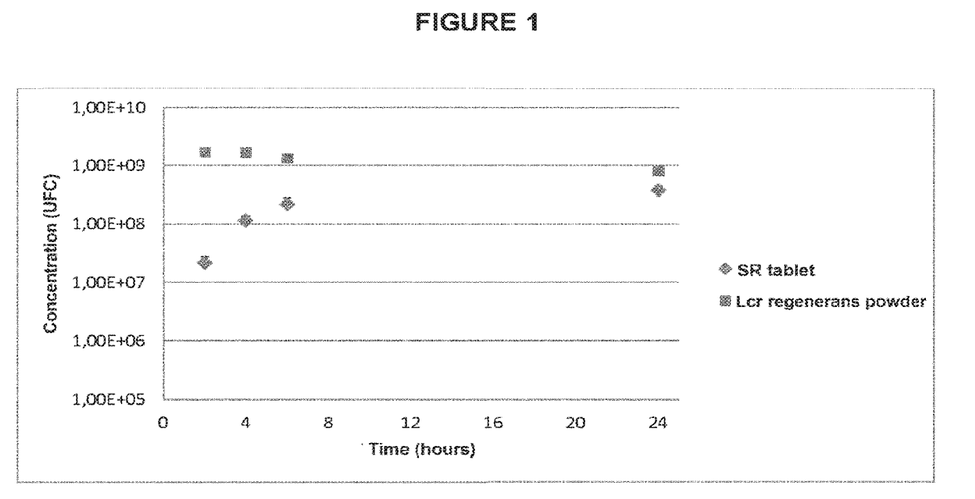
FIG. 1 represents the results of the study of the release of the Lcr35® strain from the commercial powder (Lcr Regenerans®, squares) and from the tablet according to the present invention (SR tablet, diamond).

In comparison, the SR tablet placed in the same medium releases the strain gradually and in a controlled manner (FIG. 1). This so-called controlled release is evaluated by the increase in the quantity of bacteria in the medium over the first hours of monitoring (2, 4, 6 and 24 h) to reach a maximum equivalent to the powder after 24 h. The release of the strain from the "tablet" form is controlled over the first hours in order to gradually colonize the medium to reach a threshold value (24 h) equivalent to the free powder in equal dosage. The threshold value is on the order of $10^9$ CFU in the medium.

The tablet retains its integrity for 24 h by forming a polymer matrix through which the Lcr35® strain is released. Next, a progressive erosion of the unit is observed. The release is thus prolonged until the total erosion of the tablet, which is observed after 72 h of incubation in SVF. The medium is thus saturated with *Lactobacillus*, making it possible to obtain a therapeutic effect over several days, leading to a decrease in dosage.

In the context of the present invention, a tablet can be considered "sustained-release" when a progressive release of the probiotic strain is observed (in contrast with a flash release). Particularly, a tablet can be considered "sustained-release" when a progressive release of the probiotic strain is observed during implementation of the method described above. A release can be considered progressive when it increases over a range of at least two hours during implementation of the method described above.

Growth Capacities of the Lcr35® Strain Released from the SR Tablet

A mini-fermentor (500 mL) is used as a closed chamber in order to evaluate the growth of the strain.

The medium used is MRS which is adjusted beforehand to pH 4.2 (vaginal pH). After sterilization of the experimental assembly, an SR tablet is placed in the MRS medium (250 mL) which is maintained at 37° C. and stirred at 200 rpm (impeller). Growth is monitored by regular sampling of the medium for counting after dilution on MRS agar. The sample volume is replaced with fresh medium after each sampling.

Figure 4:
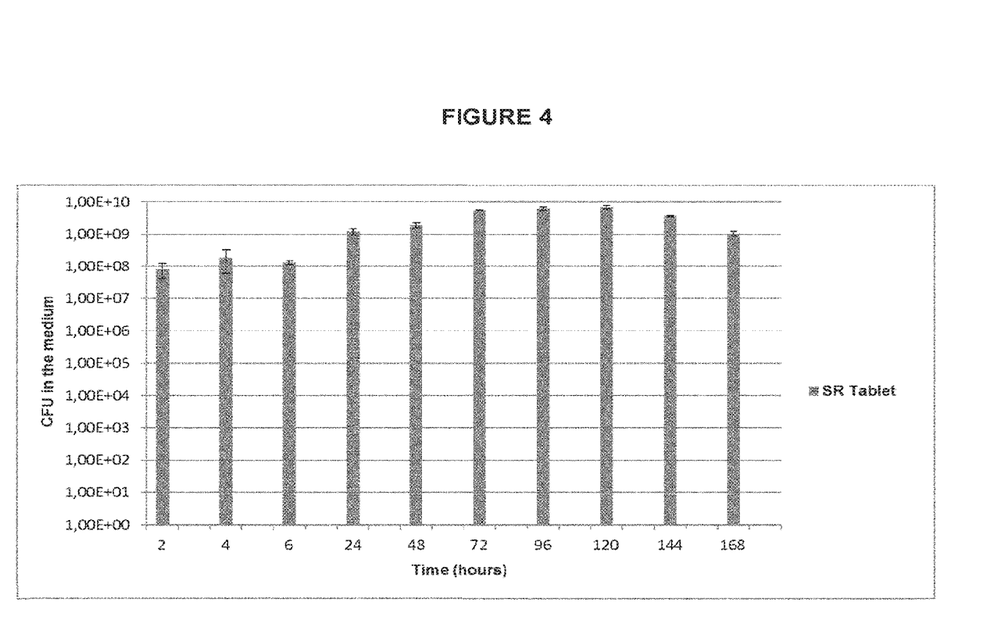
FIG. 4 represents the results of the study of the growth of the Lcr35® strain from the tablet according to the present invention: CFU in the medium at various times (expressed in hours).

The results are presented in FIG. 4. They show the capacity of the strain to regenerate and grow once released from the tablet, up to values close to $10^{10}$ CFU in the medium. This study confirms that in addition to being released from the tablet (see above), the strain retains its capacity of multiplication and colonization once in contact with a medium favorable to its development. Colonization of the medium by the strain is an element essential to obtaining the therapeutic effect on VVC and recurrent VVC but also to restoring a healthy vaginal flora.

Inhibition of the Growth of Pathogenic Strains *C. albicans* and *G. vaginalis* in Contact with the SR Tablet A certain number of in vitro and in vivo studies showed the capacity of *Lactobacillus rhamnosus* Lcr35®:
- to be implanted in the vaginal epithelium, as well as the longevity of such an implantation (Coudeyras S, Jugie G, Vermerie M, Forestier C. Adhesion of human probiotic *Lactobacillus rhamnosus* to cervical and vaginal cells and interaction with vaginosis and vaginitis-associated pathogens. 2008. Infectious diseases in obstetrics and gynecology; Coudeyras S, Jugie G, Vermerie M, Forestier C. Adhesion of the probiotic *Lactobacillus* Lcr35 to immortalized human cervical and vaginal epithelial cells, Infect Dis Obstet Gynecol. 2008; 2008: 549640);
- and to inhibit the growth of pathogenic bacteria responsible for bacterial vaginoses (*Gardnerella vaginalis* and *Prevotella bivia*) but also for mycoses (*Candida albicans*) by producing various microbicide substances (Coudeyras S, Jugie G, Vermerie M, Forestier C. Adhesion of human probiotic *Lactobacillus rhamnosus* to cervical and vaginal cells and interaction with vaginosis and vaginitis-associated pathogens. 2008. Infectious diseases in obstetrics and gynecology; A. Nivoliez, O. Camares, M. Paquet-Gachinat, S. Bornes, C. Forestier, P. Veisseire, Influence of manufacturing processes on in vitro properties of the probiotic strain *Lactobacillus rhamnosus* Lcr35®, J. Biotechnol. 160 (2012) 236-241).

The goal of developing such a form could make it possible to treat vaginal infections in both a curative and a preventive manner, such as vaginoses and more particularly VVC. To that end, the strain must be able to act on the pathogenic strain once released from the tablet.

Here, inhibition capacity is tested against the pathogenic strain: *C. albicans*. The SR tablet of said invention is placed in direct contact with a *C. albicans* culture.

To that end, a preculture of the pathogenic strain *C. albicans* is prepared in Sabouraud medium (AES, Bruz, France) at 25° C. In equivalent proportions, the preculture is brought into contact with MRS medium (Biomérieux, Marcy l'étoile, France) containing an SR tablet. A second pill box is monitored without the presence of the tablet in order to evaluate the growth of the pathogenic strain alone (*C. albicans* control).

Monitoring was carried out over 96 h at 37° C. At each inspection time (0, 2, 4, 24, 48, 72, 96 h), the pathogenic strain is counted on Sabouraud agar incubated at 25° C. for 5 days.

Figure 5:
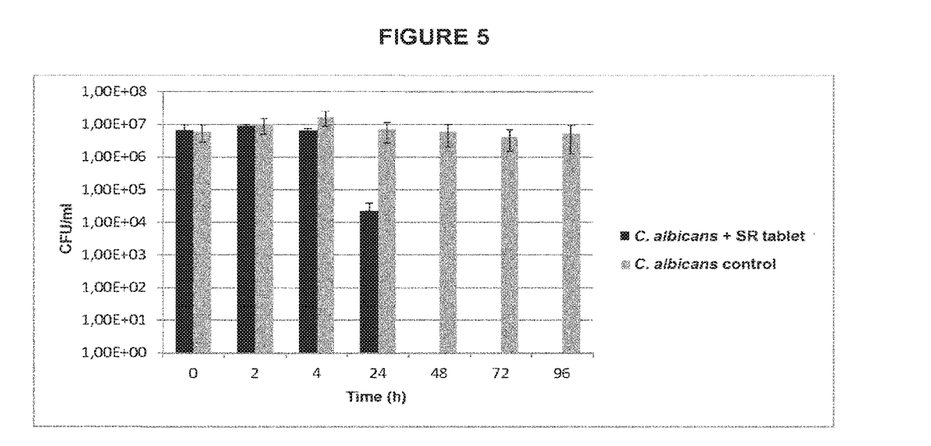
FIG. 5 represents the results of the study of inhibition of *C. albicans* growth by the Lcr35® strain from the tablet according to the present invention in direct contact: viability (CFU/mL) at various times (expressed in hours) for the control (*C. albicans*; gray) and for the tablet according to the present invention (*C. albicans*+SR tablet; black).

The results obtained are presented in FIG. 5. Contact of the SR tablet with a *C. albicans* culture allows to significantly inhibit the growth of the pathogen after 24 h, leading to its complete inhibition after 48 h of co-culture. The Lcr35® strain released from the SR tablet thus retains its pathogen inhibition capacities. By having a sustained-release of the Lcr35® strain and thus a prolonged action against the growth of the pathogen, the strain released from the tablet will then be able to be reimplanted in the vaginal cavity for the flora to return to a natural equilibrium.

Inhibition of the Growth of the Pathogenic Strain *G. vaginalis* in Contact with the SR Tablet The concentration of the pathogen (*G. vaginalis*) alone and in the presence of the *Lactobacillus rhamnosus* Lcr35 strain packaged as a sustained-release tablet was evaluated with determination of the titer at T0, T4h, T6h, T8h, T24h, T30h. The inhibition capacity of the SR tablet was evaluated by direct contact (prior culture of the pathogen and addition of an SR tablet) and following a step of preculture for the pathogen and for the strain contained in the tablet.

The culture media used for preparing the inocula and reading the titers are:
- BHI culture medium/*Gardnerella* agar for *Gardnerella vaginalis*
- MRS culture medium/MRS agar for the *Lactobacillus* strains
- the test culture medium is a homogeneous mixture of the pathogen culture medium and of MRS.

After contacting and at each sampling time, 1 mL is sampled and successive 1/10 dilutions are then prepared in tubes of sterile water. In the suitable dilutions, 1 mL is incubated in MRS agar at 37° C. for 3 days for the Lcr35 strain and 0.1 mL is inoculated on the surface of *Gardnerella* agar and placed at 37° C. for 48 h in the presence of $CO_2$ for *G. vaginalis*.

For the preparation of the control *Gardnerella vaginalis*, one places 15 mL of BHI culture medium inoculated with the pathogenic strain and 15 mL of non-inoculated MRS culture medium.

For bringing into contact the inocula, one places 15 mL of the pathogenic strain with 15 mL of inoculated MRS culture medium (preculture) or of non-inoculated MRS culture medium where one places an SR tablet (direct contact).

Monitoring times: Samples are taken and titers are determined at T0, T4h, T6h, T8h, T24h and T30h.

Figure 6:
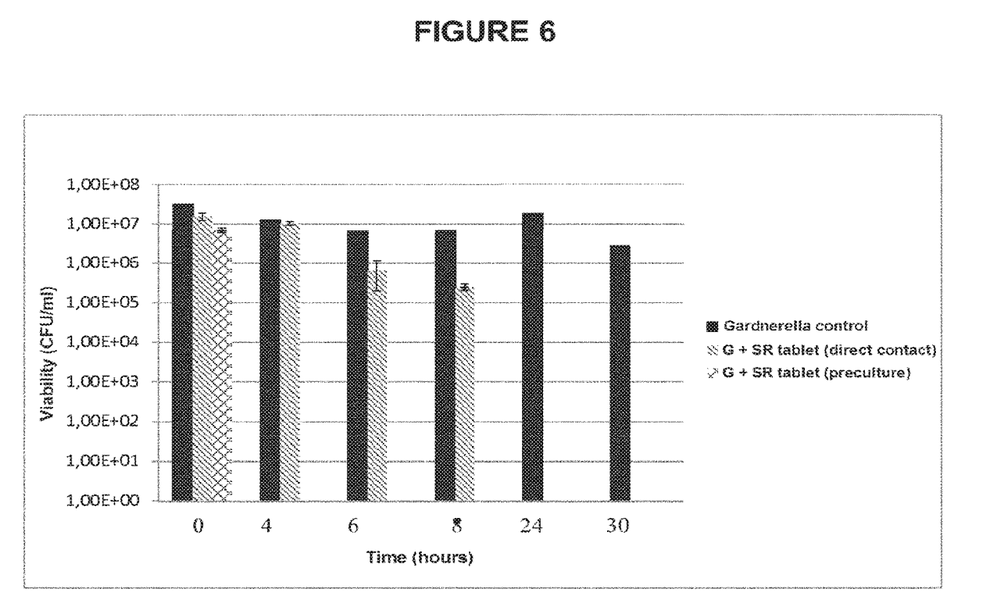
FIG. 6 represents the results of the study of inhibition of *G. vaginalis* growth by the Lcr35® strain from the tablet according to the present invention in direct contact or after a preculture phase: viability (CFU/mL) as a function of time (hours) (black: control *G. vaginalis*, hatched: *G. vaginalis*+SR tablet, direct contact; cross-hatched: *G. vaginalis*+SR tablet, preculture).

The results obtained are presented in FIG. 6. Contact of the SR tablet with a *G. vaginalis* culture allows to significantly inhibit the growth of the pathogen after 6 h, leading to its complete inhibition after 24 h of co-culture. The Lcr35® strain released from the SR tablet thus retains its pathogen inhibition capacities. By having a sustained-release of the Lcr35® strain and thus a prolonged action against the growth of the pathogen, the strain released from the tablet will then be able to be reimplanted in the vaginal cavity for the flora to return to a natural equilibrium.

Mucoadhesion of the SR Tablet

Tests were carried out on freshly excised pig vaginal walls. The protocol is as follows.

Placement of the vaginal mucous membrane and the tablet

The tests are carried out under a Microbiological Safety Hood in a sterile manner. medium (pH 4.2) is preheated to 37° C. (50 mL per sample).

A portion of vaginal mucous membrane suitable for covering the bottom of a sterile flask is taken. The bottom of the flask is covered with cyanoacrylate adhesive then the mucous membrane is arranged so as to obtain a uniform surface. The mucous membrane is wetted with SVF pH 4.2

(about 1 mL), then the tablet is placed on the mucous membrane by exerting pressure with a finger (20 seconds).

The 50 mL of preheated SVF is then poured slowly into the bottle, which is then closed again.

Test of mucoadhesion in SVF pH 4.2

The bottle is placed in a stirring rack at 75 rpm, at 37° C., until detachment of the tablet from the vaginal surface. Mucoadhesion is monitored every 30 minutes for 7 h then, after 24 h, every hour until its detachment or its complete erosion. The mucoadhesive capacity of the tablet is expressed in hours.

This protocol was applied to the SR tablet of said invention as well as to the commercial capsule. The results showed that the capsule exhibits a very limited mucoadhesion (2 h±17 min) while the mucoadhesive SR tablet adheres to the wall for a period of 21 h±1 h. The complete erosion of the tablet is also observed after 72 h of incubation (FIG. 2). The mucoadhesion parameter is a fundamental parameter in order to maintain the form in the cavity over a period sufficiently long to allow the implantation of the strain in the vaginal cavity then the inhibition of the pathogen.

The invention claimed is:

1. A mucoadhesive sustained-release vaginal tablet consisting essentially of: from $10^9$ to $10^{11}$ CFU of *Lactobacillus rhamnosus* Lcr35 per gram of tablet; and an excipient that is 10% to 30% by weight of the tablet relative to the total weight of the tablet, is suitable for conferring upon said tablet its properties of vaginal wall mucoadhesion and sustained release, and is hydroxypropylmethylcellulose with a dynamic viscosity greater than 10,000 mPa·s, wherein formation of the tablet comprises subjecting the *Lactobacillus rhamnosus* Lcr35 and said excipient to a compressive stress of from 50 to 400 MPa, resulting in maintenance of viability and sustained release of the *Lactobacillus rhamnosus* Lcr35 from the tablet and in the vaginal mucoadhesion of the tablet.

2. The tablet according to claim 1, wherein said excipient is from 10% to 20% by weight of the tablet relative to the total weight of the tablet.

3. The tablet according to claim 1 further comprising cryoprotectants, preservatives, lubricants, flow agents, binders, or diluents.

4. A method for preparing a mucoadhesive sustained-release vaginal tablet according to claim 1, the method comprising the following steps:
   a. mixing at least $10^9$ to $10^{11}$ CFU per gram of tablet of *Lactobacillus rhamnosus* Lcr35 with 10% to 30% by weight, relative to the total weight of the tablet, of hydroxypropylmethylcellulose with a dynamic viscosity greater than 10,000 mPa·s suitable for conferring upon said tablet its properties of vaginal wall mucoadhesion and sustained release; and
   b. compressing a mixture obtained in step a. with a compressive stress of 50 to 400 MPa.

5. The tablet according to claim 1, wherein the *Lactobacillus rhamnosus* Lcr35 is in a lyophilized form.

* * * * *